United States Patent [19]
Takeuchi et al.

[11] Patent Number: 5,440,063
[45] Date of Patent: Aug. 8, 1995

[54] CONCURRENT PREPARATION OF DIMETHYLCHLOROSILANE AND TRIORGANOCHLOROSILANE

[75] Inventors: Masaki Takeuchi; Akira Yamamoto; Mikio Endo; Tohru Kubota; Yasufumi Kubota, all of Niigata, Japan

[73] Assignee: Shin-Etsu Chemical Company, Limited, Tokyo, Japan

[21] Appl. No.: 335,415

[22] Filed: Nov. 3, 1994

[30] Foreign Application Priority Data

Nov. 5, 1993 [JP] Japan .................. 5-301222

[51] Int. Cl.$^6$ ................................ C07F 7/08
[52] U.S. Cl. ......................... 556/469; 556/477
[58] Field of Search ................. 556/477, 469

[56] References Cited

U.S. PATENT DOCUMENTS 4,889,838 12/1989 Lewis et al. ............. 556/469 X
5,258,535 11/1993 Ishikawa et al. .......... 556/477 X
5,312,949 5/1994 Shirahata et al. .......... 556/477

OTHER PUBLICATIONS

English Language Abstract of JP-A 53095922.
English Language Abstract of JP-B 82030114.
English Language Abstract of JP-A 56092895.
English Language Abstract of JP-A 55061195.

*Primary Examiner*—Paul F. Shaver
*Attorney, Agent, or Firm*—Birch, Stewart, Kolasch & Birch

[57] ABSTRACT

Dimethylchlorosilane and a triorganochlorosilane of the formula: $R^1R^2R^3SiCl$ wherein $R^1$, $R^2$, and $R^3$ are independently selected from monovalent hydrocarbon groups are concurrently prepared by reacting dimethyldichlorosilane with a SiH bond-containing silane compound of the formula: $R^1R^2R^3SiH$ in the presence of a Lewis acid catalyst. The method is especially effective for concomitant preparation of dimethylchlorosilane and trimethylchlorosilane or t-butyldimethylchlorosilane in an inexpensive, simple, safe manner and in high yields.

6 Claims, No Drawings

5,440,063

CONCURRENT PREPARATION OF DIMETHYLCHLOROSILANE AND TRIORGANOCHLOROSILANE

BACKGROUND OF THE INVENTION

1. Field of the Invention

This invention relates to a method for concurrently preparing dimethylchlorosilane and a triorganochlorosilane.

2. Prior Art

Dimethylchlorosilane is a monomeric source material playing an important role in the silicone industry. For example, it is used as a starting material for preparing silicone fluides and silicone resins having a Si-H bond at one end or in a backbone thereof. It is also used as an intermediate in the synthesis of organic silicon compounds such as silylating agents.

On the other hand, triorganochlorosilanes, for example, trimethylchlorosilane and derivatives thereof are not only used in a wide range of application as silylating agents, but also effective for treating inorganic materials to be hydrophobic and introducing a terminal block unit into an organopolysiloxane chain. Also t-butyldimethylchlorosilane is important as a silylating agent for the synthesis of medicines such as antibiotics and other organic compounds.

Several methods are known in the prior art for the preparation of dimethylchlorosilane. For example, when dimethyldichlorosilane is prepared by a direct process, by-products are obtained along with hydrocarbons in a low-boiling component. Dimethylchlorosilane is isolated from the by-products by distillation. This process has the drawback that dimethylchlorosilane is obtained only in a small yield despite a relatively long process time. Alternatively, dimethylchlorosilane is prepared by starting with tetramethyldisiloxane. Since tetramethyldisiloxane is prepared by cracking an oil containing a Si-H bond, the overall process is time consuming and entails the risk of cleavage of a Si-H bond during cracking.

It is reported in Kogyo Kagaku Zassi (Journal of Industrial Science), 60, 1395 (1957) to synthesize dimethylchlorosilane by reacting pentamethylchlorodisilane with dry hydrogen chloride at high temperature. Chem. Comm., 507 (1970) reports another synthesis route involving passing hydrogen chloride through polydimethylsilane under exposure of UV radiation to thereby react polydimethylsilane with hydrogen chloride. These methods use expensive reactants and are not generally acceptable in the industry.

JP-A 53-95922 discloses a method for preparing a dialkylmonochlorosilane by reducing a dialkyldichlorosilane with sodium borohydride and optionally sodium hydride in N,N,N',N',N'',N''-hexamethylphosphortriamide. However, since N,N,N',N',N'',N''-hexamethylphosphortriamide was recently found strongly carcinogenic, this method was commercially prohibited from use.

A still further method is reduction of a silicon-chlorine bond in a chlorosilane using a lithium aluminum hydride. When a dialkyldichlorosilane is reduced with such a reducing agent, both of the two chlorine atoms undergo reduction, resulting in a dialkylsilane, but not a dialkylmonochlorosilane.

For preparing trimethylchlorosilane, several methods are known in the art other than the direct method. Commonly employed is a synthetic method based on reaction involving dimethyldichlorosilane, methyltrichlorosilane or tetrachlorosilane using a Grignard reagent. This method is difficult to selectively produce only trimethylchlorosilane while a relatively large amount of tetramethylsilane is by-produced. This requires a cumbersome step of separating and purifying trimethylchlorosilane from concomitant methylsilanes at the end of reaction. In Z, Anorg. Allgem. Chem., 287, 273 (1956), an attempt was made to effect methylation reaction of tetrachlorosilane or methyltrichlorosilane using methylaluminumsesquichloride. This results in a mixture of various methylsilanes, failing to selectively produce trimethylchlorosilane as a single component.

JP-B 57-30114 discloses that trimethylchlorosilane is obtained in a compositional ratio of 81.7% by passing methylhydrogendichlorosilane and methyl chloride through metallic aluminum at 180° to 450° C. However, this method requires high temperature and suffers from the serious risk that the by-produced aluminum chloride can clog the flow system. It is also known to prepare trimethylchlorosilane by passing hydrogen chloride gas through tetramethylsilane in the presence of a Friedel-Crafts catalyst (JP-A 56-92895) and by effecting disproportionation reaction between tetramethylsilane and dimethylchlorosilane in the presence of a Friedel-Crafts catalyst (JP-A 55-61195). Since a preceding step of synthesis reaction is required to prepare tetramethylsilane which is the starting reactant, the overall process is a combination of two steps and thus less efficient.

On the other hand, t-butyldimethylchlorosilane is synthesized by chlorinating t-butyldimethylsilane with chlorine. This process fails to effectively utilize hydrogen atoms because they are lost as hydrogen chloride.

SUMMARY OF THE INVENTION

An object of the present invention is to provide a method for concurrently preparing dimethylchlorosilane and a triorganochlorosilane in an inexpensive simple manner and in high yields without a danger.

The inventors have found that by reacting dimethyldichlorosilane with a SiH bond-containing silane compound of the formula: $R^1R^2R^3SiH$ wherein $R^1$, $R^2$, and $R^3$ are independently selected from monovalent hydrocarbon groups in the presence of a Lewis acid catalyst, only one of the Si-Cl bonds of the dimethyldichlorosilane is converted into a Si-H bond to thereby form dimethylchlorosilane and simultaneously, a triorganochlorosilane of the formula: $R^1R^2R^3SiCl$ wherein $R^1$, $R^2$, and $R^3$ are as defined above is obtained in high yields and in an inexpensive, simple, safe manner. This method is effective for concomitantly preparing dimethylchlorosilane and trimethylchlorosilane. The method also permits dimethylchlorosilane and t-butyldimethylchlorosilane be produced concomitantly by effectively utilizing the hydrogen atom of t-butyldimethylsilane.

Accordingly, the present invention provides a method for concurrently preparing dimethylchlorosilane and a triorganochlorosilane of the formula: $R^1R^2R^3SiCl$ wherein $R^1$, $R^2$, and $R^3$ are independently selected from monovalent hydrocarbon groups, comprising the step of reacting dimethyldichlorosilane with a SiH bond-containing silane compound of the formula: $R^1R^2R^3SiH$ wherein $R^1$, $R^2$, and $R^3$ are as defined $R^3$ above in the presence of a Lewis acid catalyst.

DETAILED DESCRIPTION OF THE INVENTION

The method of the invention starts with a SiH bond-containing silane compound of the general formula: $R^1R^2R^3SiH$. $R^1$, $R^2$, and $R^3$ are independently selected from monovalent hydrocarbon groups, preferably having 1 to 20 carbon atoms, more preferably 1 to 10 carbon atoms, for example, alkyl groups such as methyl, ethyl, propyl, isopropyl, n-butyl, t-butyl, cyclohexyl, cyclopentyl and n-octyl, and aryl groups such as phenyl. The R groups may be identical or different. Exemplary silane compounds include trimethylsilane, triethylsilane, t-butyldimethylsilane, phenyldimethylsilane, isopropyldimethylsilane, dicyclohexylmethylsilane, n-octyldimethylsilane, n-butyldimethylsilane, and cyclopentyldimethylsilane.

Exemplary Lewis acid catalysts include aluminum chloride, iron chloride, boron trichloride, zinc chloride, cesium chloride, cobalt chloride, nickel chloride, titanium tetrachloride, tin chloride, rhodium chloride, cadmium chloride, and acetylacetonatocopper. Aluminum chloride is most preferred.

Preferably, the SiH bond-containing silane compound is used in an amount of 0.25 to 1.5 mol, more preferably 0.5 to 1 mol per mol of dimethyldichlorosilane. Less than 0.25 mol of the silane compound on this basis would leave a large proportion of the reactant unreacted. More than 1.5 mol of the silane compound would allow for formation of a by-product, tetramethylsilane.

The Lewis acid is preferably used in an amount of 0,001 to 0.5 mol, more preferably 0.02 to 0.1 mol per mol of dimethyldichlorosilane. Less than 0.001 mol of the Lewis acid on this basis would result in a substantial lowering of reaction rate whereas more than 0.5 mol of the Lewis acid would allow undesirable disproportionation reaction to take place such as cleavage of Si-C bonds.

The reaction is generally carried out by dissolving a Lewis acid catalyst in dimethyldichlorosilane, adding a SiH bond-containing silane compound of $R^1R^2R^3SiH$ thereto, and agitating the reaction mixture.. The reaction temperature is preferably about 0° to 70° C., more preferably about 20° to 40° C. The reaction time generally ranges from about 10 minutes to about 2 hours.

If desired, the reaction may be carried out in a solvent. A choice is preferably made of the solvents which are not reactive with dimethyldichlorosilane and/or the SiH bond-containing silane compound. Typical solvents are toluene, ethyl acetate, decane, and o-xylene.

At the end of reaction, dimethylchlorosilane is isolated from the reaction solution by distillation, preferably after the Lewis acid has been deactivated. For example, 1 to 5 mol of ether per mol of the Lewis acid is added for such deactivation. Exemplary ethers are anisole, diphenyl ether, o-dimethoxybenzene, and p-dimethoxybenzene.

EXAMPLE

Examples of the invention are given below by way of illustration and not by way of limitation.

Example 1

A four-necked flask was equipped with a condenser, thermometer, dropping funnel, and stirrer was charged with 12.9 g (0.10 mol) of dimethyldichlorosilane and 0.27 g (0.002 mol) of AlCl₃, which were agitated with the stirrer. To the flask at room temperature, 5.8 g (0.05 mol) of triethylsilane was added dropwise over 30 minutes. Thereafter, agitation was continued for one hour while the flask was kept at 30° C. 0.28 g (0,002 mol) of o-dimethoxy-benzene was added to the reaction solution which was agitated for a further one hour. Dimethylchlorosilane and triethylchlorosilane were isolated from reaction solution by distillation. There were obtained 3.78 g of dimethylchlorosilane and 7.37 g of triethylchlorosilane in a yield of 80% and 98%, respectively.

Example 2

Example 1 was repeated except that 10.0 g (0.1 mol) of isopropyldimethyisilane was used instead of 5.8 g of triethylsilane. There were obtained 8.7 g of dimethylchlorosilane and 13.4 g of isopropyldimethylchlorosilane in a yield of 92% and 98.5%, respectively.

Example 3

A four-necked flask equipped with a condenser, thermometer, gas feed tube, and stirrer was charged with 129.1 g (1.0 mol) of dimethyldichlorosilane and 1.3 g (0.01 mol) of AlCl₃, which were agitated with the stirrer. To the flask at room temperature, trimethylsilane which had been synthesized in a separate flask from methylmagnesium chloride and 57.5 g (0.5 mol) of methyldichlorosilane was fed. Agitation was continued for one hour. 2.2 g (0.02 mol) of anisole was added to the reaction solution which was agitated for a further one hour. Dimethylchlorosilane and trimethylchlorosilane were isolated from the reaction solution by distillation. There were obtained 42.0 g of dimethylchlorosilane and 48.9 g of trimethylchlorosilane in a yield of 89% and 90%, respectively.

Example 4

A four-necked flask equipped with a condenser, thermometer, gas feed tube, and stirrer was charged with 129.1 g (1.0 mol) of dimethyldichlorosilane, 100 ml of toluene, and 1.3 g (0.01 mol) of AlCl₃, which were agitated with the stirrer. To the flask at room temperature, trimethylsilane which had been synthesized in a separate flask from methyl-magnesium chloride and 57.5 g (0.5 mol) of methyldichlorosilane was fed. Agitation was continued for one hour. 2.8 g (0.02 mol) of o-dimethoxybenzene was added to the reaction solution which was agitated for a further one hour. Dimethylchlorosilane and trimethylchlorosilane were isolated from the reaction solution by distillation. There were obtained 42.6 g of dimethylchlorosilane and 47.3 g of trimethylchlorosilane in a yield of 90% and 87%, respectively.

Example 5

A four-necked flask equipped with a condenser, thermometer, dropping funnel, and stirrer was charged with 129.1 g ( 1.0 mol ) of dimethyldichlorosilane and 1.3 g (0.01 mol) of AlCl₃, which were agitated with the stirrer. To the flask at room temperature, 58.2 g (0.5 mol) of t-butyldimethylsilane was added dropwise over one hour. Thereafter, agitation was continued for one hour while the flask was kept at 30° C. 2.8 g (0.02 mol) of o-dimethoxybenzene was added to the reaction solution which was agitated for a further one hour. Dimethylchlorosilane and t-butyldimethylchlorosilane were isolated from the reaction solution by distillation. There were obtained 42.8 g of dimethylchlorosilane and 69.0 g of t-butyldimethylchlorosilane in a yield of 91% and 92%, respectively.

Example 6

A four-necked flask equipped with a condenser, thermometer, dropping funnel, and stirrer was charged with 129.1 g (1.0 mol) of dimethyldichlorosilane, 1.3 g (0.01 mol) of AlCl$_3$, and 75.3 g of toluene, which were agitated with the stirrer. To the flask at room temperature, 58.2 g (0.5 mol) of t-butyldimethylsilane was added dropwise over one hour. Thereafter, agitation was continued for one hour while the flask was kept at 30° C. 3.4 g (0.02 mol) of diphenyl ether was added to the reaction solution which was agitated for a further one hour. 2.8 g (0.02 mol) of o-dimethoxybenzene was added to the reaction solution which was agitated for a still further one hour. By distillation of the reaction solution, there were obtained 42.8 g of dimethylchlorosilane and 142.5 of a 50% toluene solution of t-butyldimethylchlorosilane in a yield of 91% and 95%, respectively.

There has been described a method for concurrently preparing dimethylchlorosilane and a triorganochlorosilane in an inexpensive, simple, safe manner and in high yields. The method is especially effective for concomitant preparation of dimethylchlorosilane and trimethylchlorosilane or t-butyldimethylchlorosilane.

Japanese Patent Application No. 5-301222 is incorporated herein by reference.

Although some preferred embodiments have been described, many modifications and variations may be made thereto in the light of the above teachings. It is therefore to be understood that within the scope of the appended claims, the invention may be practiced otherwise than as specifically described.

We claim:

1. A method for concurrently preparing dimethylchlorosilane and a triorganochlorosilane of the formula: R$^1$R$^2$R$^3$SiCl wherein R$^1$, R$^2$, and R$^3$ are independently selected from monovalent hydrocarbon groups, comprising the step of:
   reacting dimethyldichlorosilane with a SiH bond-containing silane compound of the formula: R$^1$R$^2$R$^3$SiH wherein R$^1$, R$^2$, and R$^3$ are as defined above in the presence of a Lewis acid catalyst.

2. The method of claim 1 wherein the triorganochlorosilane is used in an amount of 0.25 to 1.5 mol per mol of dimethyldichlorosilane.

3. The method of claim 1 wherein the Lewis acid is used in an amount of 0,001 to 0.5 mol per mol of dimethyldichlorosilane.

4. The method of claim 1 wherein the reaction is carried out at about 0° to 70° C.

5. A method for concurrently preparing dimethylchlorosilane and trimethylchlorosilane, comprising the step of:
   reacting dimethyldichlorosilane with trimethylsilane in the presence of a Lewis acid catalyst.

6. A method for concurrently preparing dimethylchlorosilane and t-butyldimethylchlorosilane, comprising the step of:
   reacting dimethyldichlorosilane with t-butyldimethylsilane in the presence of Lewis acid catalyst.

* * * * *